A. D. Reeves,
Catamenial Sack,
No. 3,023. Reissued July 7, 1868.
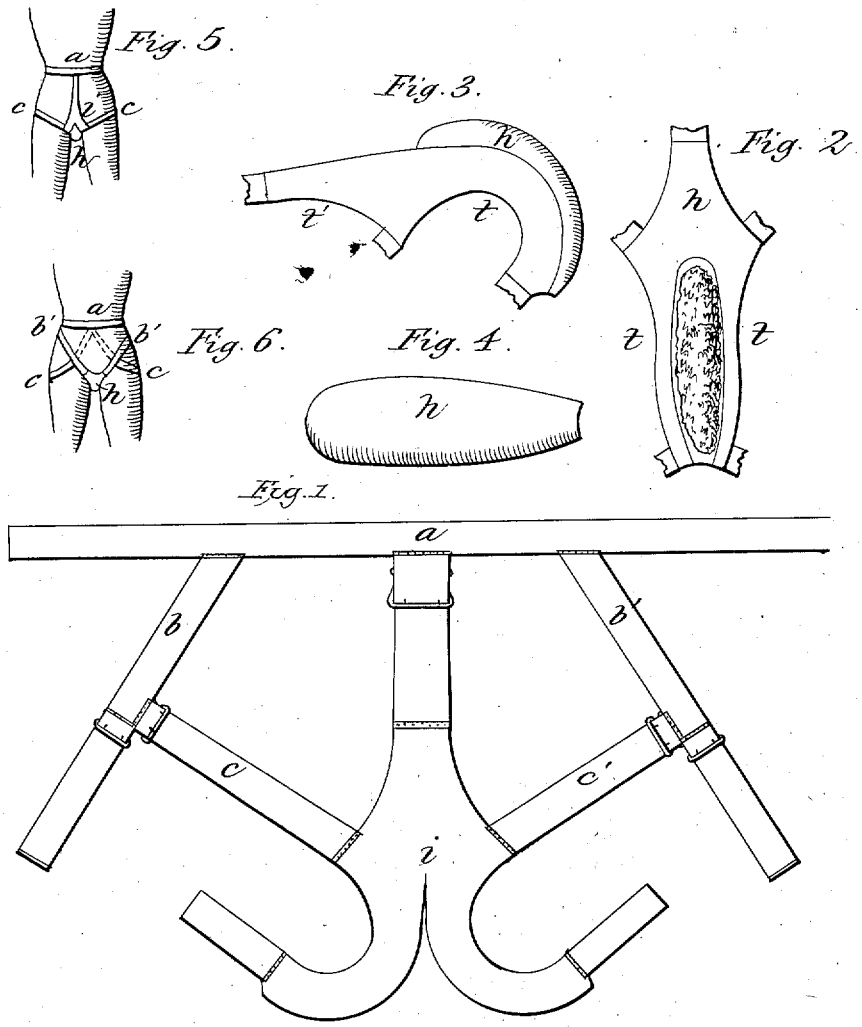
Witnesses:
Henry C. Houston
Wm Frank Seavey
Inventor:
A. D. Reeves
per Wm Henry Clifford Atty

UNITED STATES PATENT OFFICE.

ALEXANDER D. REEVES, OF PORTLAND, MAINE.

IMPROVEMENT IN FEMALE SUPPORTERS.

Specification forming part of Letters Patent No. 34,845, dated April 1, 1862; Reissue No. 3,023, dated July 7, 1868.

*To all whom it may concern:*

Be it known that I, ALEXANDER D. REEVES, of Portland, in the county of Cumberland and State of Maine, have invented a new and useful Improved Truss, &c.; and I hereby declare the following to be a full, clear, and exact description thereof, which will enable others to make and use my invention, reference being had to the accompanying drawings, forming part of this specification, in which—

Figure 1 is a view on the inside of the straps or supports of my invention. Fig. 2 is a top view of the sack. Fig. 3 is a side view of the same. Fig. 4 is a bottom view of the same. Fig. 5 is a back view of a form with my invention applied thereto. Fig. 6 is a front view of the same.

The purpose of this invention is to produce a truss and sack for such use by both males and females, as the sex of the wearer may require.

It consists, first, of a combination of straps or braces and a belt to support and keep in place a sack; and, second, of a sack to serve as a catamenial sack for females, and a support for males.

In the accompanying drawings, *a* shows the belt to encompass the waist; *b b'* show braces running down in front or on the abdomen, with the lower end of which braces is connected the sack *h*. At the center of the belt *a*, at the back, is attached the strap *d*, which runs vertically down the back, and also connects with the sack *h*. Where this strap passes the cleft of the nates it is made broad, as at *i*, to prevent it from working into the same and producing discomfort. The straps *c* and *c'* keep the part *i* in proper condition. The straps *c* and *c'* intersect with the front braces, *b b'*, at such position as to keep them easy for the wearer and allow free motion to the lower limbs. This is illustrated in the view in Fig. 1, where the straps are shown in place. The sack *h* passes through the perinæum and up to the pubes in front, where it joins the front braces, *b b'*, and is thus held in its place. *c* and *c'* at the back pass over the prominences of the ischium, as illustrated in the back view, Fig. 2, then around the hips to the front, and, as before described, intersect the front braces, *b b'*. (See also Fig. 1.)

If desired, the braces *c c'* can be carried up and connected with the belt in front, so as to further sustain the said straps. *h* is the sack, made concave within, as illustrated in Fig. 4, so as to contain a sponge when used during periodicity by females, and to support and contain the private parts of males. The sponge can be placed in the hollow or concavity of the sack.

Thus a truss is produced easy to wear, not irksome to the body, and one which allows of a free motion of the limbs and still keeps the sack *h* in place during all positions of the body. It can, of course, be adjusted to different sizes of the frame by buckles. The sack is made of rubber. Perfect ease in the perinæum in the wearing of the sack is imparted by its peculiar form, as indicated in the drawings, with the curved parts *t t'*, to conform to the limbs and form. To illustrate this, I refer to Figs. 2 and 3. From the description it will be seen that the invention is both a scrotal and catamenial suspensory.

What I claim as my invention, and desire to secure by Letters Patent, is—

The sack *h*, made as and for the purposes herein set forth, and supported by the belt and braces, arranged as herein described.

A. D. REEVES.

Witnesses:
WM. H. CLIFFORD,
HENRY C. HOUSTON.